United States Patent
Caplan et al.

(10) Patent No.: US 10,019,542 B2
(45) Date of Patent: Jul. 10, 2018

(54) SCORING A POPULATION OF EXAMPLES USING A MODEL

(71) Applicant: PTC Inc., Needham, MA (US)

(72) Inventors: Ryan Todd Caplan, Huntingdon Valley, PA (US); Bruce F. Katz, Philadelphia, PA (US); Joseph John Pizonka, Phoenixville, PA (US)

(73) Assignee: PTC Inc., Needham, MA (US)

( * ) Notice: Subject to any disclaimer, the term of this patent is extended or adjusted under 35 U.S.C. 154(b) by 0 days.

(21) Appl. No.: 15/306,925

(22) PCT Filed: Apr. 14, 2016

(86) PCT No.: PCT/US2016/027538
§ 371 (c)(1),
(2) Date: Oct. 26, 2016

(87) PCT Pub. No.: WO2016/168464
PCT Pub. Date: Oct. 20, 2016

(65) Prior Publication Data
US 2017/0046460 A1 Feb. 16, 2017

Related U.S. Application Data

(60) Provisional application No. 62/147,326, filed on Apr. 14, 2015.

(51) Int. Cl.
*G06F 17/50* (2006.01)
*G06F 17/00* (2006.01)
(Continued)

(52) U.S. Cl.
CPC .......... *G06F 17/5009* (2013.01); *G06F 17/00* (2013.01); *G06F 17/18* (2013.01);
(Continued)

(58) Field of Classification Search
CPC .. G06F 17/5009; G06F 9/5066; G06F 9/4881; G06F 17/00; G06F 17/18;
(Continued)

(56) References Cited

U.S. PATENT DOCUMENTS

2005/0246105 A1 11/2005 Faber et al.
2009/0062144 A1 3/2009 Guo
(Continued)

FOREIGN PATENT DOCUMENTS

WO 2011008361 A1 1/2011
WO WO-2011008361 A1 * 1/2011 ............. G06N 5/025

OTHER PUBLICATIONS

International Search Report dated Aug. 25, 2016 (dated Aug. 25, 2016) in corresponding International Patent Application No. PCT/US2016/027538.

*Primary Examiner* — Omar F Fernandez Rivas
*Assistant Examiner* — Justin C Mikowski
(74) *Attorney, Agent, or Firm* — Pepper Hamilton LLP (57) ABSTRACT

A computer-implemented method for scoring an example with causal information includes a computer system receiving an indication of a goal and applying a predictive model to the example to yield an output score with respect to the goal. The computer system produces causal score for each feature-value pair in the example, each causal score indicating of a relative extent to which the feature-value pair is responsible for influencing the output score. Then, the computer system presents the output score and the causal score for each feature-value pair in the example.

12 Claims, 8 Drawing Sheets

(51) Int. Cl.
  *G06F 17/18* (2006.01)
  *G06Q 10/06* (2012.01)
  *G06Q 30/02* (2012.01)
  *G06F 19/00* (2018.01)

(52) U.S. Cl.
  CPC ............ *G06F 19/30* (2013.01); *G06Q 10/06* (2013.01); *G06Q 10/06393* (2013.01); *G06Q 30/02* (2013.01); *G06Q 30/0201* (2013.01); *G06Q 30/0202* (2013.01)

(58) Field of Classification Search
  CPC ........... G06F 19/24; G06F 19/30; G06N 5/02; G06Q 10/06; G06Q 10/06393; G06Q 30/02; G06Q 30/0201; G06Q 30/0202
  See application file for complete search history.

(56) References Cited

U.S. PATENT DOCUMENTS

| | | | |
|---|---|---|---|
| 2011/0225103 A1 | 9/2011 | Clarke et al. | |
| 2011/0302031 A1* | 12/2011 | Chen | G06Q 30/0255 |
| | | | 705/14.53 |
| 2012/0316833 A1* | 12/2012 | Lovick | G06F 17/5009 |
| | | | 702/179 |
| 2013/0166188 A1 | 6/2013 | Zheng et al. | |
| 2014/0163951 A1 | 6/2014 | Nikoulina et al. | |
| 2014/0215487 A1 | 7/2014 | Cherkasova et al. | |
| 2014/0278754 A1* | 9/2014 | Cronin | G06F 17/30539 |
| | | | 705/7.29 |
| 2015/0026035 A1 | 1/2015 | Showalter | |

* cited by examiner

SCORING A POPULATION OF EXAMPLES USING A MODEL

CROSS-REFERENCE TO RELATED APPLICATIONS

This application is a national phase filing under 35 U.S.C. § 371 of International Patent Application No. PCT/US2016/027538 filed Apr. 14, 2016, which claims the benefit of U.S. Provisional Application Ser. No. 62/147,326 filed Apr. 14, 2015, each of which is incorporated herein by reference in its entirety.

TECHNICAL FIELD

The present disclosure relates generally to methods, systems, and apparatuses, for using predictive models to score a population of users. The disclosed techniques may be applied, for example, to analyze past customer behavior in order to predict or influence future (or otherwise unknown) behaviors.

BACKGROUND

Predictive analytics refers to the algorithmic process of analyzing a set of feature-value pairs, referred to herein as "examples," in order to make predictions about future, or otherwise unknown, events. This process is applicable to many different types of data. For example, the features included in each example may be ordinal (in which case the value is a number), nominal (which case the value is a string), or Boolean (with values of true and false or 0/1). Thus, predictive analytics may be applied in almost any area in which knowledge of historical data is available. For example, in the business context, past customer behavior may be analyzed with predictive analytics to optimize existing customer relationship processes, identify unexpected opportunities, and anticipate future issues.

The primary tool for predictive analytics is a predictive model which identifies relationships between different features in the historical data. This model may be any structure that takes an example and applies an algorithm to produce a resultant output number or category. A predictive model may be a man-made model, a machine-generated model, or an ensemble model that takes the results of sub-models and combines these results. Once created, the predictive model may be applied to new conditions in order to predict or influence future, or otherwise unknown events through a process referred to herein as "scoring." More specifically, scoring is the process of taking a predictive model, an example set of data points, and optionally additional parametric and other defining conditions or factors, and producing a resultant score for each provided example. The score is the prediction of the model for the supplied example.

Conventional predictive models employ scoring schemes which are relatively basic. Typically, the only information provided is a single probability of a particular event or behavior, or more generally, an output value corresponding to the supplied example. Thus, it is desirable to expand and enhance conventional scoring techniques by including other forms of analysis to include, for example, an identification of variable features that maximize or minimize a particular goal outcome, causal conditions for a particular resource, and/or feature attributes that optimize resource expenditure.

SUMMARY

Embodiments of the present invention address and overcome one or more of the above shortcomings and drawbacks, by providing methods, systems, and apparatuses related to the process of scoring using predictive models.

According to some embodiments, a computer-implemented method for scoring an example with causal information includes a computer system receiving an indication of a goal and applying a predictive model to the example to yield an output score with respect to the goal. The computer system produces a causal score for each feature-value pair in the example, each causal score indicating a relative extent to which the feature-value pair is responsible for influencing the output score. Then, the computer system presents the output score and the causal score for each feature-value pair in the example.

In one embodiment of the aforementioned method, the causal score for each feature-value pair in the example is produced by determining additional output scores corresponding to all possible instantiations of values for the feature-value pair and determining a maximal difference between the output score and the additional output scores. The causal score for the feature-value pair is then the maximal difference. Additionally, the method may further include a calculation of multivariate causal determination. For example, the joint influences of a feature-value pair with the other feature-value pairs in the example may be computed and Shapley values may be generated based on these multivariate feature-value pairs. A single measure of causal influence may then be computed based on the Shapley values.

Other embodiments of the aforementioned method for scoring an example with causal information may include additional refinements or other modifications. For example, in one embodiment, a user-specified objective to maximize a goal value as an indicator of causal influence of the feature-value pair is received. Then, the computer system implementing the method determines a minimal goal value over all values of the example using the predictive model, as well as a difference between the output score and the minimal goal value. This difference may then be designated as the causal score. Conversely, in other embodiments, a user-specified objective to minimize a goal value as an indicator of causal influence of the feature-value pair is received. In this case, the computer system determines a maximal goal value over all values of the example using the predictive model and a difference between the output score and the maximal goal value. This difference is then designated as the causal score for the feature-value pair.

Additionally, in some embodiments of the aforementioned method for scoring an example with causal information, the example comprises a plurality of unordered features. In these embodiments, the method may further include determining an attribute output score for each attribute included in the plurality of unordered features and determining an attribute causal score for each attribute included in the example based on a maximal difference between the attribute causal score corresponding to the attribute and attribute output scores corresponding to other attributes included in the example.

According to some embodiments, the aforementioned method, with or without the additional features set forth above may be used to implement a system for scoring an example with causal information. For example, in one embodiment, such a system comprises one or more processors, a non-transitory, computer-readable storage medium in operable communication with the one or more processors, and a display. The computer-readable storage medium contains one or more programming instructions that, when executed, cause the processors to apply a predictive model to the example to yield an output score with respect to a goal and produce a causal score for each feature-value pair in the example. As with the method discussed above, each causal score indicates the relative extent to which the feature-value pair is responsible for influencing the output score. The display in the system is configured to present the output score and the causal score for each feature-value pair in the example.

According to other embodiments, a computer-implemented method for scoring a population of examples subject to an additional constraint of a fixed aggregate resource expenditure includes a computer system creating a master gain ratio list and processing each example in the population of examples using an iterative process. This iterative process includes identifying a plurality of attribute combinations associated with the example, using a predictive model to determine a plurality of gain ratios, each gain ratio corresponding to a distinct one of the plurality of attribute combinations, identifying a particular attribute combination in the plurality of attribute combinations having a largest gain ratio, and adding the particular attribute combination and the largest gain ratio to the master gain ratio list. The computer system sorts master gain ratio list according to the gain ratio and presents the master gain ratio list on a display. In some embodiments, prior to presenting the master gain ratio list, the computer system may remove any item from the master gain ratio list corresponding to a resource expenditure exceeding a predetermined constraint. In some embodiments, the population of examples comprises a plurality of continuous feature values and the method comprises binning the plurality of continuous feature values into equal intervals, yielding a plurality of bins. The iterative process is applied to each of the plurality of bins.

The iterative process performed in the aforementioned method may include additional features in different embodiments. For example, in one embodiment, the iterative process further comprises determining a cost for each feature in the example that varies according to a feature type associated with the feature and for each of the plurality of attribute combinations, adjusting the gain ratio based on the cost associated with features in the attribute combination. In another embodiment, the iterative process further comprises determining a cost for each individual value associated with feature-value pairs included in the example and for each of the plurality of attribute combinations, adjusting the gain ratio based on the cost corresponding to values associated with feature-value pairs in the attribute combination. Additionally, in other embodiments, the iterative process further comprises using, for each of the plurality of attribute combinations, a cost function associated with achieving and not achieving a goal to determine a goal probability estimation. The gain ratio associated with each attribute combination may then be adjusted based on the corresponding goal probability estimation.

According to some embodiments, the aforementioned method for scoring a population of examples subject to an additional constraint of a fixed aggregate resource expenditure, with or without the additional features set forth above, may be used to implement a system. For example, in one embodiment, such a system comprises one or more processors, a non-transitory, computer-readable storage medium in operable communication with the one or more processors, and a display. The computer-readable storage medium contains one or more programming instructions that, when executed, cause the processors to create a master gain ratio list and process each example in the population of examples using the iterative process (discussed above). The display is configured to present the master gain ratio list.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

Systems, methods, and apparatuses are described herein which relate generally to various techniques for scoring a population of examples using predictive models. Four scoring paradigms are discussed herein: standard scoring, prescriptive scoring, causal scoring, and resource scoring. Each form of scoring provides different insights into the population and allows for tailoring of various parameters to analyze different aspects of the examples. For example, standard scoring provides a basic prediction for the population. Prescriptive modeling is similar to standard scoring, but also considers the effect of a set of features with values that vary or float (referred to as "lever features"). Causal scoring provides information regarding the relative extent to which that feature is responsible for producing or influencing the standard output score. Finally resource scoring allows resource constraints to be analyzed in the context of the predictive model to determine how a goal value can be maximized or minimized given a particular set of such constraints. Each of these scoring types may be applied independently or in a combined form to produce a multi-dimensional predictive analysis of the population.

Figure 1:
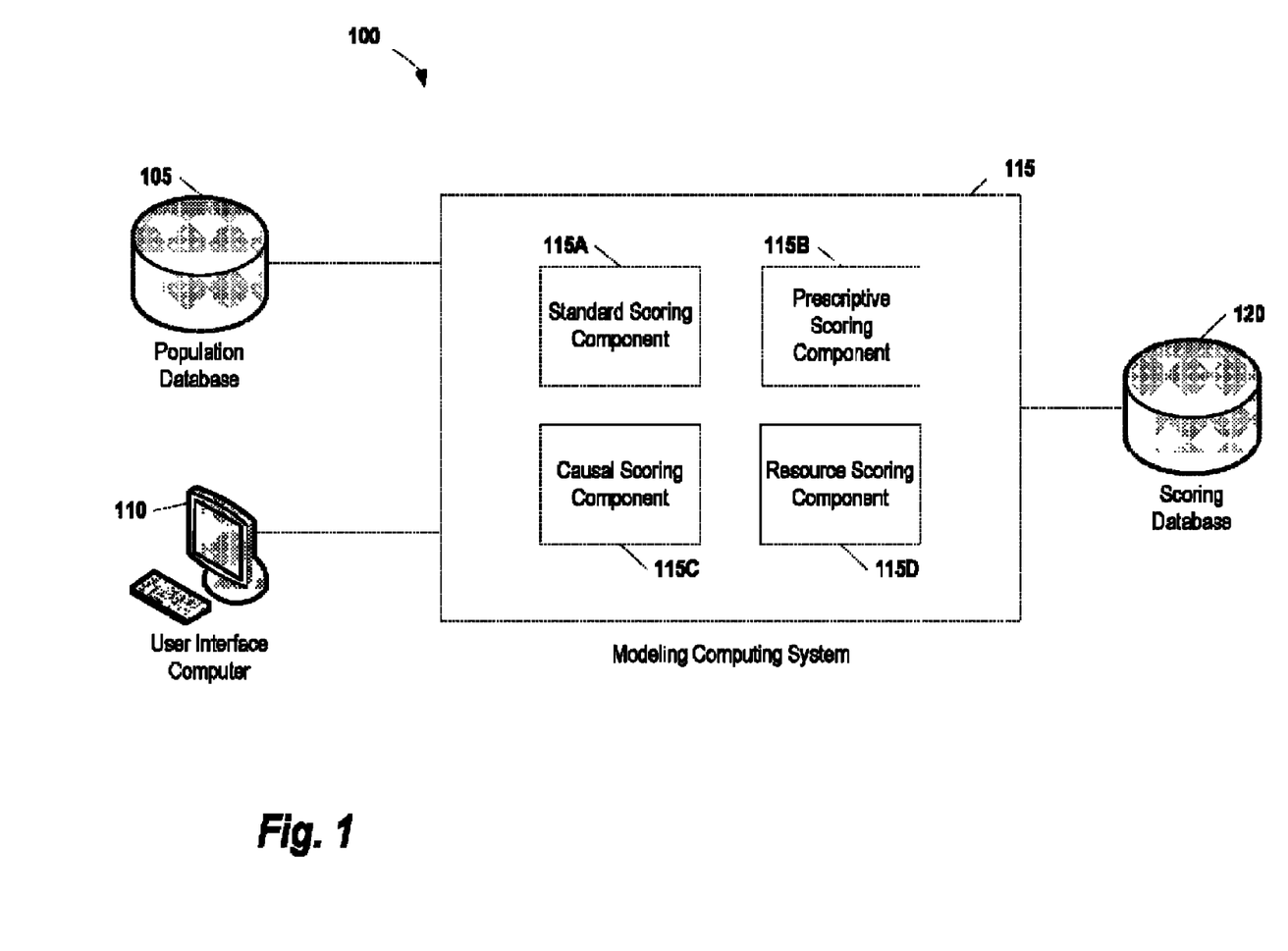
FIG. 1 provides an overview of a system for generating scoring data for a population of examples, according to some embodiments.

FIG. 1 provides an overview of a system 100 for generating scoring data for a population of examples, according to some embodiments of the present invention. Briefly, the system 100 applies one or more predictive models to a population of examples to score each example in order to predict or influence future events. The system 100 includes a Modeling Computing System 115 operably coupled to a Population Database 105 and a User Interface Computer

110. Based on input received from the User Interface Computer 110, the Modeling Computing System 115 retrieves population datasets from the Population Database 105 and processes those datasets using a variety of components (described in further detailed below) to generate scoring information in a Scoring Database 120 or displayed, with or without additional information, on the User Interface Computer 110 (see the description of FIG. 8 below for more information on how data may be presented on the User Interface Computer 110). In some embodiments, the User Interface Computer 110 may be used to specify the type of scoring that should be applied (e.g., conventional, prescriptive, causal, and/or resource). In other embodiments, the type of scoring is automatically selected based on, for example, the type of examples provided in the population.

The Standard Scoring Component 115A applies a predictive model to an example and produces a prediction of the model for that example. This prediction may be a number in the case of an ordinal goal or a category in the case of a nominal goal. To illustrate standard scoring, three examples of standard scoring are now provided, corresponding to a Boolean goal, a nominal goal, and an ordinal goal, respectively. In the first example, a predictive model constructed from a set of prior customers indicating whether they have cancelled service ("churned") on the basis of demographics and past product usage generates an output goal value for a set of future customers of true (i.e., will cancel the service) or false (i.e., will not cancel the service). Models thus constructed (for example logistic regression and neural network models) however, may also assign a number between 0 and 1 for each individual customer, indicating the relative likelihood of this event occurring for that specific customer. In the second example, a predictive model is created that takes the chemical signature of a wine and produces a regional appellation. Here the outputs are not numbers but categories such as Burgundy, Chianti, and Napa Valley. In the third example, the predictive model generates the first year revenue of a new store location for a particular franchise based on area demographics, experience of the franchisee, etc. Here the output of the model is an ordinal value, and scoring will likewise produce a numerical value.

The Prescriptive Scoring Component 115B takes as input an example as in standard scoring, and also takes a set of features that can be varied (i.e., "lever features"). The Prescriptive Scoring Component 115B then produces the values or setting for each of the lever features that maximize or minimize a particular goal outcome or probability of that outcome occurring based on user or system preferences or settings. The table below illustrates how prescriptive scoring may be used:

| Levers | Fixed features |
| --- | --- |
| #phone_calls deal_offered | age gender income . . . |

In this example, the lever features are the two features #phone_calls (an ordinal) and deal_offered (a Boolean). These lever features have been shown by modeling to affect the rate of churn. Other features may vary, but are not lever features as they cannot be altered by the agent attempting to minimize customer cancellations. The aim of prescriptive scoring is to find the discrete values of the lever features that will maximize or minimize a goal. Note that, in general, the optimal values of the lever features will depend on the values of the fixed features, thus a search process may be employed (see FIG. 3).

The Causal Scoring Component 115C applies a predictive model as in Standard scoring to an example and produces a discrete value for each of the features in that example indicating the relative extent to which that feature and its corresponding current value is responsible for producing or influencing the output score. The table below illustrates an example of causal scoring. It is often desirable to know not only the score that a predictive model produces for a given example, but also to better understand or explain the reason for that score. Causal scoring is designed to gauge the relative extent to which each of the feature-value pairs in a given example is responsible for a given resultant goal value or prediction score. For example, a predictive model could predict that a patient has the relatively high probability of 23% of having a heart attack in the next 3 years. The table gives the relative strength of each of the five most important determinants of this score:

| Feature | Value | Causal scores |
| --- | --- | --- |
| Diabetes | true | .29 |
| Smoking | heavy | .17 |
| Cholesterol (LDL) | 250 | .12 |
| Weekly exercise | 3 hours | .05 |
| Age | 57 | .03 |

Note that each patient will be associated not only a unique standard score, but also with a unique set of causal scores for each feature. Moreover, the ordering of features will in general be different for each. A patient of given age, ethnicity, and gender, for example may have a high relative probability of a heart attack because they are a heavy drinker; another patient with different fixed attributes may have a similar risk but for a completely different set of reasons. Finally, the fact that the particular value of a feature influences risk does not necessarily mean that the feature can be manipulated to provide a better result. For example, in the above table, age cannot be altered and diabetic status, to a lesser extent, also cannot be changed.

The Resource Scoring Component 115D applies a predictive model to a set of examples, a set of lever features, and an overall resource constraint over those features to produce prescriptive scores for each example such that the aggregate goal value is maximized or minimized within these constraints based on the user or system preferences or settings. Thus, it provides an indication of how to distribute finite resources over a population in order to maximize the aggregate result, given that the model is already built. As an example of resource scoring, consider a company instituting a multi-channel marketing campaign with two primary channels, physical mail and phone calls. Suppose further there is the possibility of contacting a potential customer multiple times through each channel, but the number of contacts for each channel is strictly limited, and a different limit is in effect for each channel. For example, it may be possible to send only a total of 3 emails and make 4 phone calls per customer. Furthermore, aggregate constraints may also be in effect, say 1500 emails and 1000 total phone calls over all customers. A predictive model will yield the expected gain for each combination of numbers of contact over the channels, but in itself will not tell one how best to allocate the limited number of resources. For example, if the model predicts that contacting customer A with 2 emails and 3 phone calls yields an expected gain of $1.26, and 5 emails and 3 phone calls to customer B gives a gain of $1.57, who should be contacted first, and how much resources should be devoted to this contact? As described below with regards to FIG. 7, resource scoring maximizes the ratio of the expected gain over the resources required to achieve that gain.

It should be noted that the components 115A, 115B, 115C, and 115D illustrated in FIG. 1 are only a sampling of the different components that may be included in the Modeling Computing System 115. In some embodiments, the functionality corresponding to these components can be merged and/or supplemented with additional functionality. Additionally, in other embodiments, the Modeling Computing System 115 may include additional components that provide additional modeling functionality not described herein.

Figure 2:
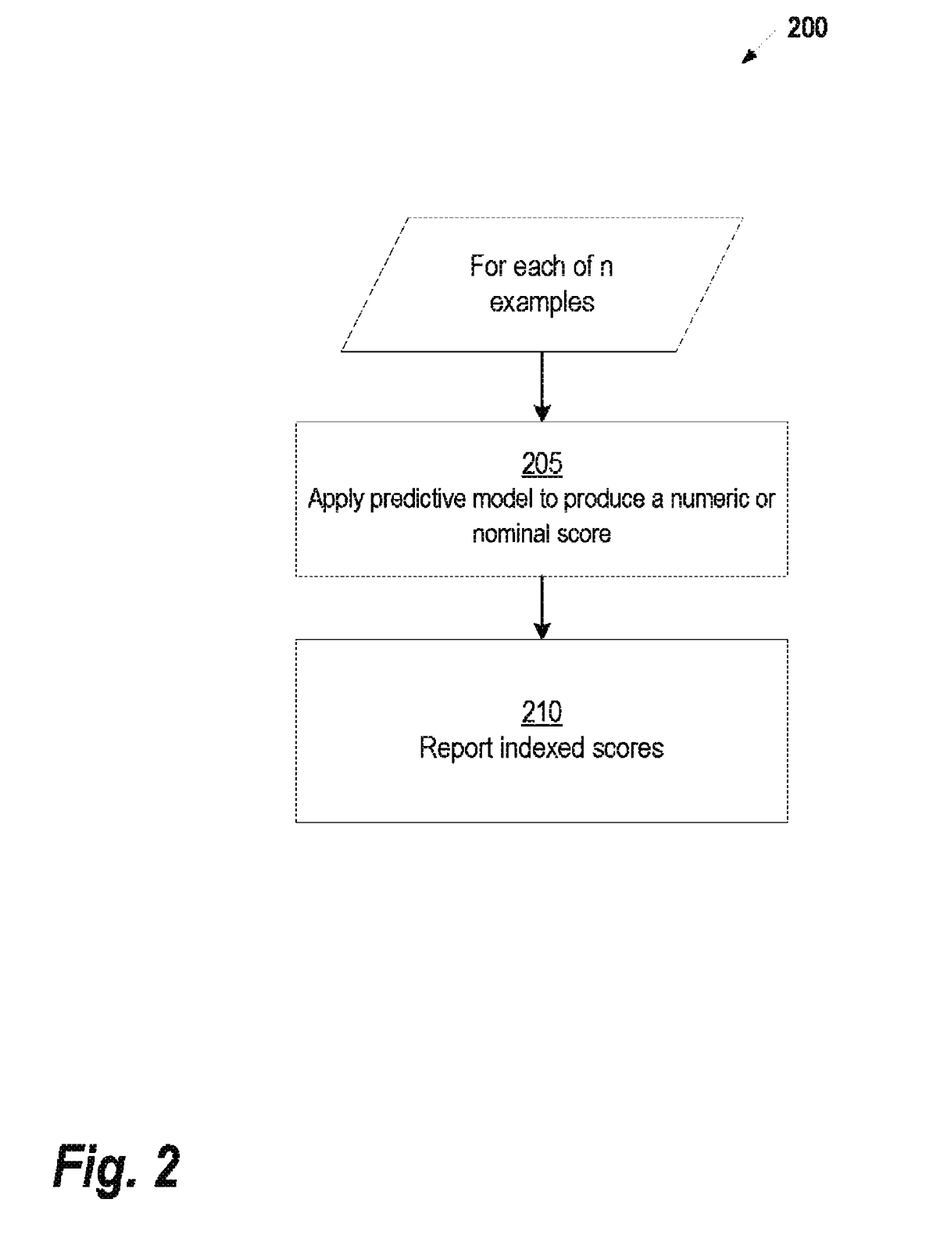
FIG. 2 provides a process for standard scoring, according to some embodiments.

FIG. 2 provides a process 200 for standard scoring, according to some embodiments. Standard scoring applies a predictive model to an example and produces a number in the case of an ordinal goal or a category in the case of a nominal goal. This number or category value is the resultant prediction of the model for that example. In the example FIG. 2, the process of standard scoring is performed in a loop, where each of n examples is processed iteratively. At step 205, a predictive model is applied to the example to produce a numeric or nominal score, as appropriate. In this example, each example of the population is scored individually. However, in other embodiments, where the population includes a large number of examples, the entire population may be scored at once. Then, at step 210, the indexed scores are reported.

When the score for a Boolean goal feature is presented as a number (typically between 0.0 and 1.0), there is often a desire to reconvert these values back into either "FALSE" and "TRUE" values instead of mathematical ranges, in order to make a definitive decision for each example. In some embodiments, this is realized by inserting a threshold into this range, and making every output below this threshold false and above the threshold true, with the goal of determining the optimal threshold whereby the system minimizes false positive and false negative results while it maximizing true positive and true negative results. Once this is accomplished, a so-called confusion matrix emerges, as shown in the table below. Each of the four cells, true positives, false negatives, false positives, and true negatives will contain an integer indicating how many examples from the examples set contain the indicated properties.

|  |  | Predicted | |
| --- | --- | --- | --- |
|  |  | true | false |
| Actual | true | true positives | false negatives |
|  | false | false positives | true negatives |

In some embodiments, thresholding is carried out by maximizing a function over these four quantities, such as the Matthews correlation coefficient. In another embodiment, an additional "cost function" is associated with each cell and it is optimized accordingly. For example, if a prescription drug has relatively few side effects but is salutary in the case of a particular disease, it may be prudent to give more weight to accurate diagnoses (true positives) and discount the possibility of diagnosing someone with the disease who is in fact disease-free (false positives). In this way, additional consideration can be given to penalize or reward false negatives, and so forth, beyond the direct calculation of minimizing all false positive and false negative results while maximizing all true positive or true negative results.

In some embodiments, the standard scoring process is parallelized for execution across multiple processors. The entire process of standard scoring and its sub-processes can easily be parallelized because there is no dependency between examples. That is, if there are n examples to be scored, and m processors, the example set can be subdivided into n/m equally sized sets, and sent to the respective processor for analysis. Once scores are produced on each processor, they can be aggregated in a final step for reporting purposes.

Standard scoring by automatic methods provides the most direct use of predictive models. The generated scores provide actionable intelligence via the predicted goal value. For example, customers that are determined likely to cancel service can be targeted with special treatment including proactive outreach with marketing or pricing offers through various channels such as emails, phone contact, or other means with the goal of making the customer less likely to leave the given service.

Figure 3:
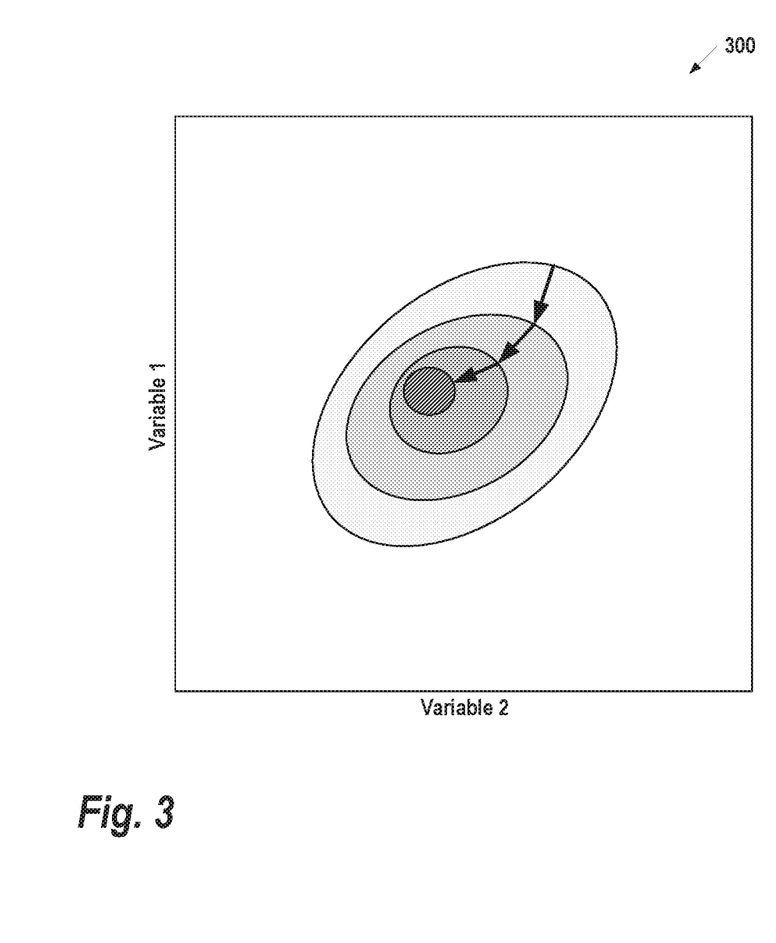
FIG. 3 provides a visualization of the process of prescriptive scoring, according to some embodiments.

FIG. 3 provides a visualization 300 of prescriptive scoring, according to some embodiments. In particular, this visualization 300 shows a hypothetical goal space as a function of two variables. Prescriptive scoring is, in essence, a multivariate maximization problem. The example of FIG. 3 shows the natural solution for two ordinal variables. However, generalization to more than two variables follows directly from the proposed algorithm. Additionally, generalization to nominal and Boolean variables is discussed below. In this example, ovals represent lines of equivalent goal values. The goal values in this case are generated by the predictive model. The starting position is at the head of the first arrow. By following a procedure of gradient descent, the algorithm is able to find a local maximum, as generally known in the art. In general, the search space as shown in FIG. 3 is not known in advance. Therefore, in practice, it may be necessary to explore each variable in small positive and negative increments to determine its effect on the goal. Movement is directed towards increments that improve this utility, proportional to the degree of improvement. This is done successively over each variable, and until the goal value stops improving. It should be noted that, while the example of FIG. 3 describes the use of gradient descent in prescriptive scoring, other optimization algorithms can be applied in different embodiments to perform a similar analysis of the underlying dataset.

Figure 4:
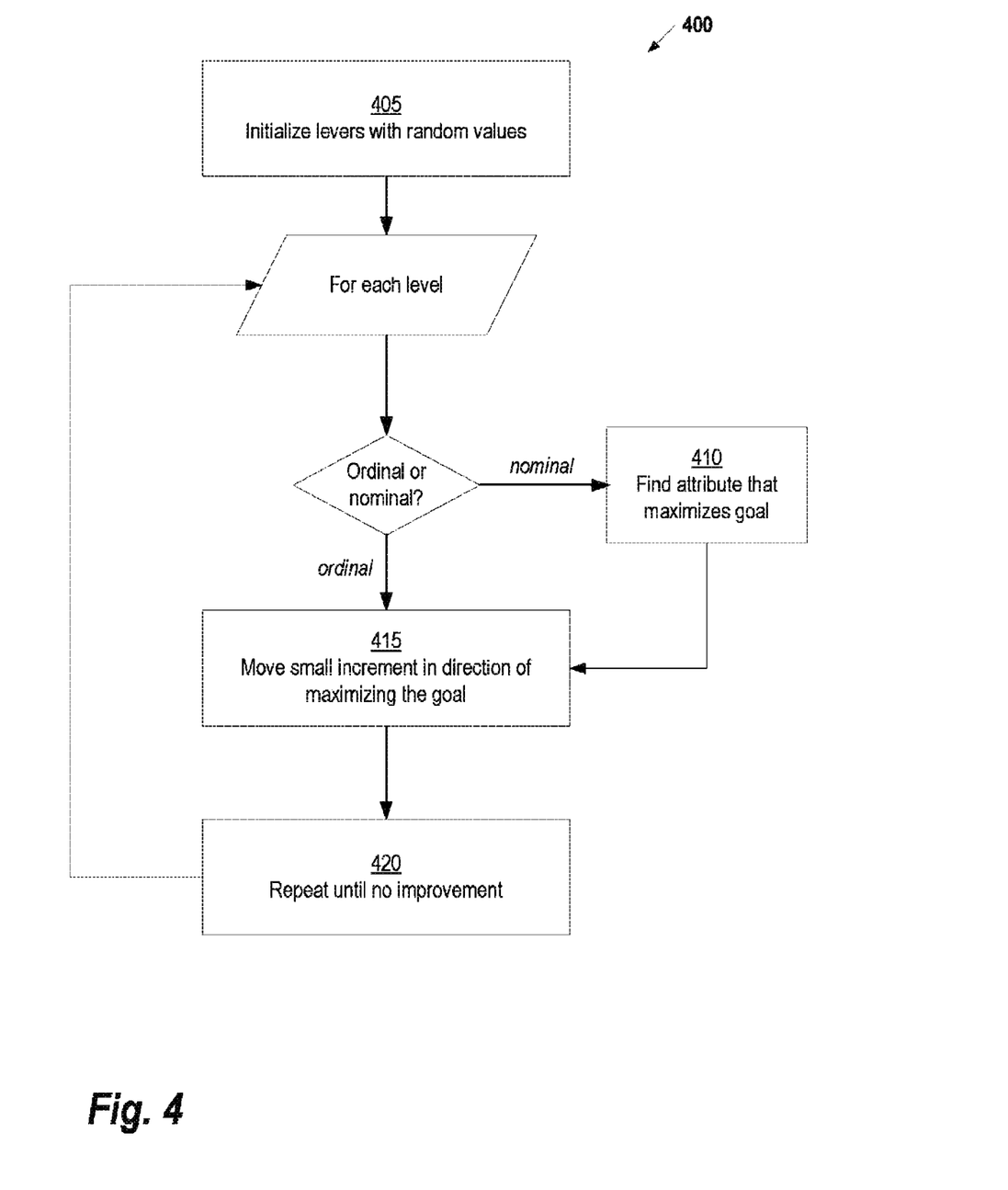
FIG. 4 provides a process for prescriptive scoring, according to some embodiments.

FIG. 4 provides a process 400 for prescriptive scoring, according to some embodiments. At step 405, lever features are initially set to random values. The algorithm iterates over each such lever in an attempt to improve the goal value. If the lever is a nominal, at 410, the algorithm chooses the best nominal attribute given the current setting of all other levers and other fixed (i.e. non-lever) features. If the feature is an ordinal, at step 415, the algorithm moves a small increment in the direction of improving the goal. As shown in 420, the process repeats until no more improvement is possible.

The technique discussed above in reference to FIGS. 3 and 4 is guaranteed to converge on maximal utility if the increments are sufficiently small. However, this guarantee applies to local maxima only. It is possible that there are one or more other global maxima of better utility somewhere else in the search space, and likely when more than two lever features are present. One method of increasing the chances of finding these global (or better) maxima is to run the algorithm multiple times with different starting points; i.e., different initial random feature settings. The final result will then be the best result for these points of entry. Regardless of the number of entry points, the output of algorithm is not only the goal value, but also the values of the lever features needed to achieve this value. The latter informs user how to act in order to achieve the desired result.

A Boolean lever feature for prescriptive scoring may be treated as a nominal with two attributes (true and false), and thus is not considered separately here.

The algorithm for prescriptive scoring above discussed with reference to FIGS. 3 and 4 is "frictionless" in that assumes that the states of all lever features can be achieved with the same cost. This will not necessarily be the case. For example, it may cost significantly more to contact a customer by phone than by email. In some embodiments, these considerations are incorporated into the search by the creation of an ROI utility function. This function will include not only the normalized cost of the goal, but also the cost of each of the lever feature needed to achieve that goal value. This methodology will ensure that lower cost methods will be favored over higher cost methods of achieving the same or similar goal value.

In broadest terms, the goal of the prescriptive scoring is not only to predict the future, as in standard scoring, but also to influence that future in a desired direction (alter the predicted future outcome result). This presumes that the lever features in the model have at least some influence on some of the examples some of the time and, in general, this will be the case. In addition, the normal caveats regarding predictive modeling apply, namely, that the model is accurate in both predicting the goal values on examples as well as generalizing to examples it has not seen and, in addition, the data is relatively stationary over time; prescriptive scoring with a weak model in general will also generate poor prescriptions.

Figure 5:
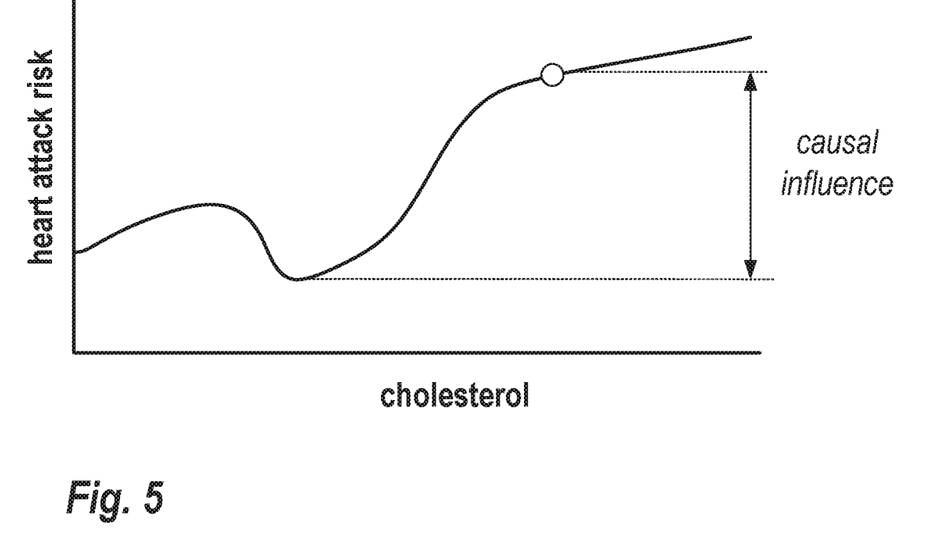
FIG. 5 provides an example of evaluating causal scoring, as it may be applied in some embodiments.

FIG. 5 provides an example of causal scoring, as it may be applied in some embodiments. Causal scoring applies a predictive model to an example and produces a discrete value for each of the features in that example indicating the relative extent to which that feature is responsible for producing or influencing the output score. The influence of a given feature with a particular value can be assessed in a counterfactual manner; that is, by asking what would happen to the prediction if this value were not the case. More specifically, this result can be obtained by comparing the current goal value with the maximal difference in the goal value as the feature is perturbed over all possible values and the corresponding model output is generated.

The example FIG. 5 illustrates maximal difference in the goal value for the case of the influence of cholesterol on heart attack risk. The dot marks the current cholesterol level and the current risk level. Lowering the cholesterol levels from this level will first decrease and then slightly increase risk. The degree of causal influence is marked by the interval between the minimal risk and the current risk, as shown on the right. This interval represents the gain in risk that this level of cholesterol induces relative to the risk if the optimal level of cholesterol was achieved, and thus the influence of this lipid concentration. Curves such as those shown in the figure are also idiosyncratic to each patient, and depend on the values of all of the fixed, non-lever features for that patient. Hence, as desired, each patient will differ in the manner in which cholesterol influences their risk score, and accordingly each will have a unique causal score for this feature.

Figure 6:
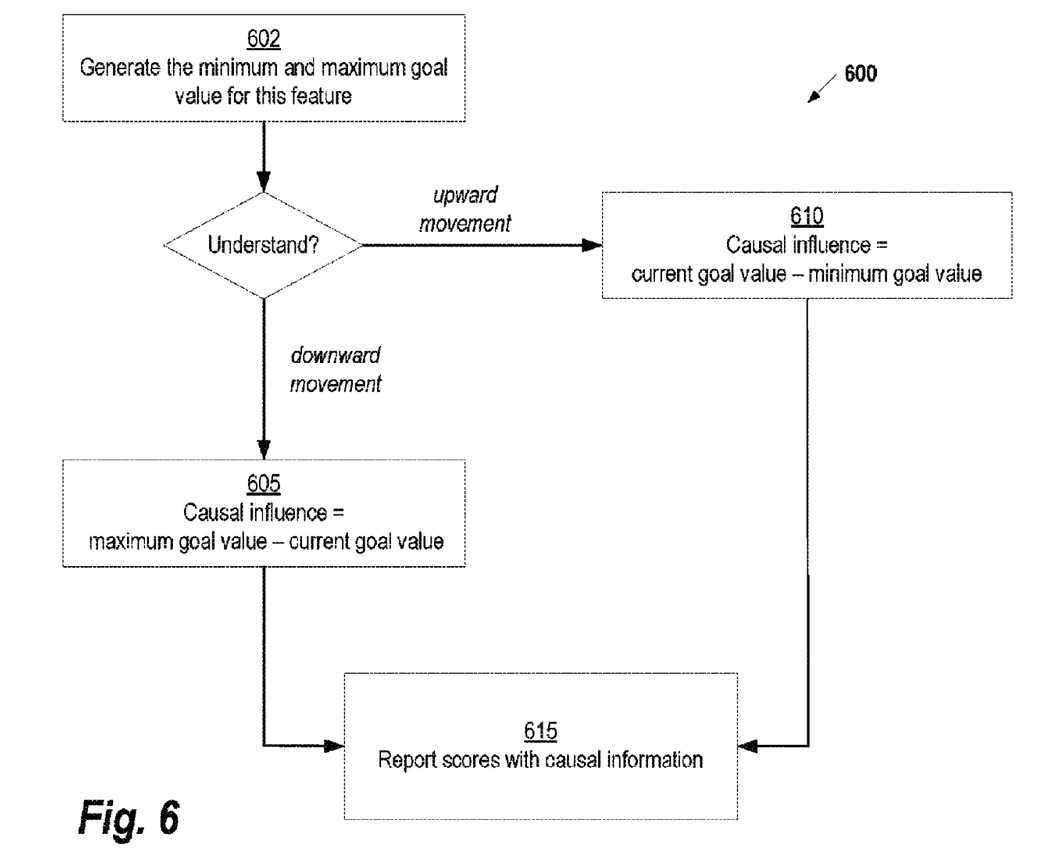
FIG. 6 provides an example of a causal scoring process, according to some embodiments.

FIG. 6 provides an example of a causal scoring process 600, according to some embodiments. This process 600 captures the two cases of significance: a) where the aim is to understand what is driving the goal value upwards, and b) where the aim is to understand what is driving the goal value downwards. In both cases, the computed causal influence will be the degree to which the feature's current value takes one in the direction of the desired understanding, relative to the maximal distance from that point over all possible feature values. For downward movement, at step 605 the causal influence is found by subtracting the current goal value from the maximum goal value. For upward movement, at step 610 the causal influence is found by subtracting the minimum goal value from the current goal value. Both cases depend on a prior calculation of minimum or maximum goal value, respectively, at step 602. This can be accomplished, for example, by iterating over successive small increments over the entire range of values or ordinal values, applying the resultant example to the model, and storing the best and worst resulting goal value. At step 615, the score, along with causal information is reported as the output of the model.

The causal scoring process 600 shown in FIG. 6 can easily be extended to the case of unordered variables. In some embodiments, instead of searching for the maximal difference over the implied range of values, the search is over the set of feature attributes. For example, if the feature is gender and the attributes are male and female, the causal influence is the difference between goal value given the current gender and the one produced by the model if the gender were to be changed to its opposite. In the case of multiple attributes, the causal influence is the greatest difference produced in the goal between the current attribute and all other attributes The causal scoring process 600 provides an estimate of the influence of a single feature at a time on a given outcome. It may be the case, however, that although the perturbation of a feature by itself reveals relatively little influence, in combination with other features influence is much greater. To assess this, in some embodiments, the causal scoring process 600 is modified try all combinations of features (up to n at a time), and then Shapley values are used to combine the various effects, 1 at a time, 2 at a time, etc. up to n at a time. Depending on n, this will entail considerably more computational resources, but may provide a more accurate assessment of influence in a complex multivariate environment.

The utility of causal scoring is best contrasted with ordinary measures of causal determination that indiscriminately apply to the population as a whole. For example, medical science may have determined that cholesterol is general is a high risk factor for heart disease in the population as a whole. But this will not necessarily be the case for a particular patient. It could be, for example, that occupation, age, and exercise mitigate this risk, in which case dietary or drug control of circulatory cholesterol levels is unnecessary. In this sense, causal scoring presents a set of complementary information to prescriptive scoring: the latter tells one what one needs to do to induce an improvement over current circumstances, while the former tells one the reason(s) why current conditions prevail.

Figure 7:
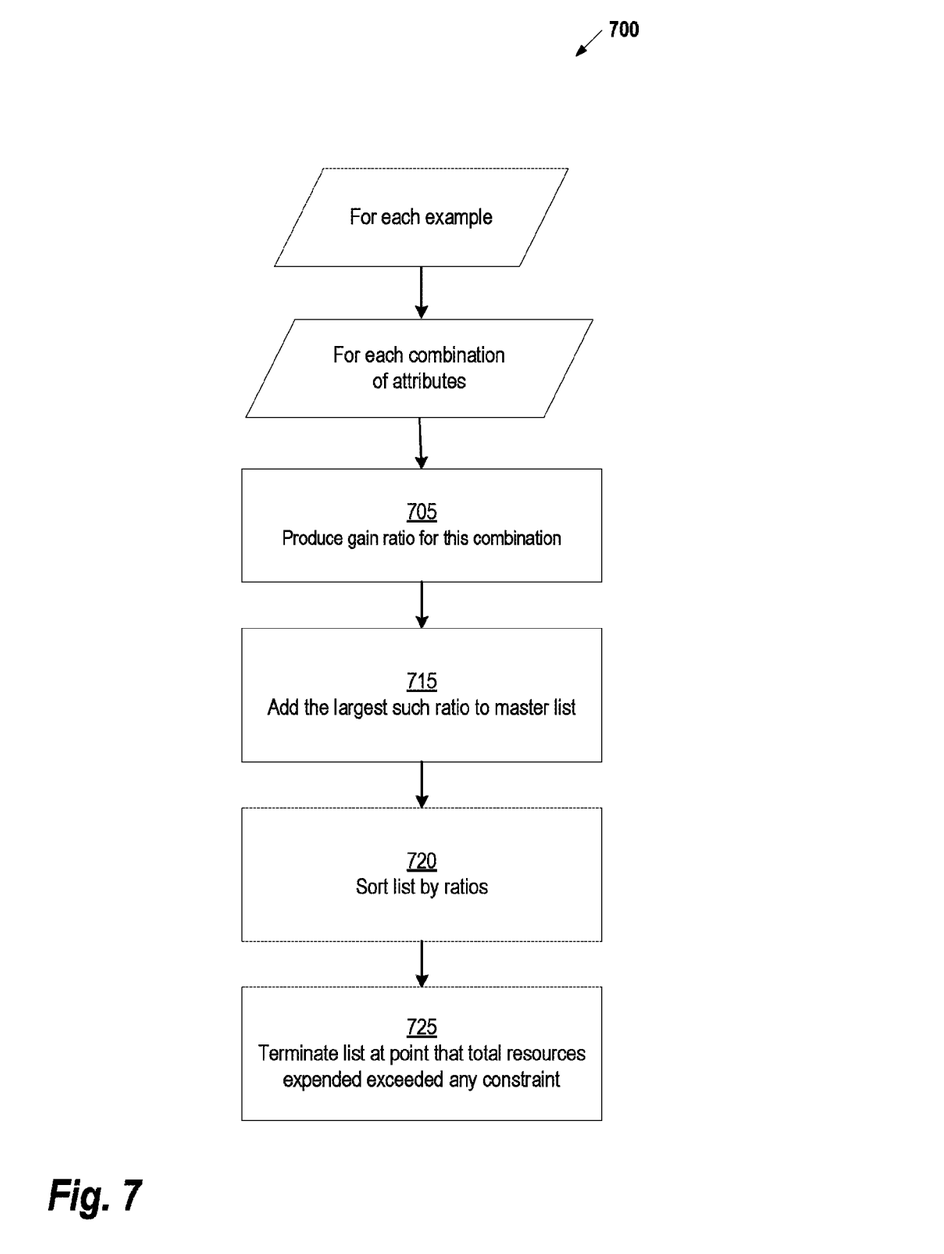
FIG. 7 provides an example of a resource scoring process, according to some embodiments.

FIG. 7 provides an example of a resource scoring process 700, according to some embodiments. In general, the goal of resource scoring is twofold. The first is to produce an order of contact, or other relevant action. The second related goal is to allocate resources for this event, and to additionally show the expected effect of this event on the goal value. Thus the goal is not simply to find the best combination of lever features for each individual record, but to find these combinations under the constraint of fixed total resources; maximizing each record will not in general provide the overall aggregate best solution because it may take too many resources to achieve this effect.

FIG. 7 shows a process 700 for resource allocation according to some embodiments where, for each example, each combination of attributes for the example is processed. This process 700 continues with the previously discussed example of resource scoring, where a company is instituting a multi-channel marketing campaign with two primary channels, physical mail and phone calls. At step 705, a gain ratio is determined for the current combination. The gain ratio is defined as the total gain for a given set of attributes, as generated by scoring the examples with these attributes set accordingly, divided by the total resources expended, relative to the baseline goal value produced by doing nothing (0 emails and 0 phone calls in this example). At step 715, the best such ratio for each example is added to a master list. Then, at step 720, this list is then sorted by gain ratio. Finally, at step 725, the list is terminated at the point that resources are exhausted for any of the lever features. In effect, the algorithm favors examples in which the greatest gain for the least amount of effort or cost is expended, and produces an ordered set of these examples within the bounds of available resources. This greedy algorithm has in practice been found to yield close to optimal performance in a number of domains. For each example and each combination of lever features attributes a gain ratio is produced. For example, if one could send up to 3 emails, and 2 phone calls per customer, the ratio for the 6 possible combinations of emails and calls would be generated.

Note that in the examples of resource scoring presented thus far, lever features were integers. This provides a natural way of examining the combinations over all lever features: simply check all possible combinations of integer values. In the case of continuous ordinal lever features this is impossible as there will be infinite possibilities for a single lever feature alone. One strategy for overcoming this is to convert such lever features to integer features by binning. For example, assume that marketing spend can be varied per customer, with an overall aggregate limit of $100K, and an individual limit of $100. The algorithm above can be used without modification if this limit is broken into 10 equal bins of $10 apiece. It is also possible to apply standard search techniques over the ordinal range to determine a more fine-grained estimate of the optimal benefit to cost ratio; for example, instead of simply indicating that the best ratio occurs between a spend of between $30 and $40, the algorithm could find the best results occur at $32.75.

In many resource scoring cases, the fundamental resource constraint will not be delimited by lever feature but by an overarching cost function, most likely in monetary terms but possibly including other factors. A marketing campaign may be allotted a fixed dollar amount, for instance, but be agnostic to channel limitations. In this situation, if the individual lever features can be expressed in the same units then the strategy of choosing the best ratios can again be used. For example, if we assume that up to 5 physical letters can be sent, and up to 8 phone calls, and that each bulk letter costs 0.27, but each phone call $3, then each of the 8×5=40 combinations will have a unique cost associated with it, and the denominator in the ratio calculation will reflect this cost. In this case, all things being equal, the algorithm will favor letter contacts over phone calls because of the large cost discrepancy.

An even more general case of resource scoring is presented when each individual example is associated with its own cost as a function of this example's constituent features. For example, it may be more costly to send a package to Alaska than to Illinois. The main algorithm can be retained, however, if these differential costs can be assumed to be computed by an external function supplied to the algorithm. The cost per example per combination is then inserted into the denominator of the ratio to form the expected gains.

Another general case of resource scoring arises when the model output itself is subject to differential costs. For example, suppose the model generated the probability of churn. The cost of losing a high revenue customer, however, may exceed that of losing a low revenue customer, even if the latter's probability of churn can be brought down with relatively little effort. In this case, the standard algorithm may be retained if the numerator of the gain ratio reflects this differential. For example, this could be calculated in this case as the product of the decrease in probability of churn and the revenue (or profitability) of the customer.

In the case of resource scoring with a large number of lever features, for example, in a multi-channel marketing campaign with many channels, it may prove too computationally expensive to examine every combination for every example: the number of such combinations will be the product of the number of possibilities in each lever. Standard heuristic search techniques such as gradient descent can be substituted for the exhaustive search proposed by the standard algorithm to produce a quasi-optimal ratio for each example and therefore a quasi-optimal aggregate solution.

Figure 8:
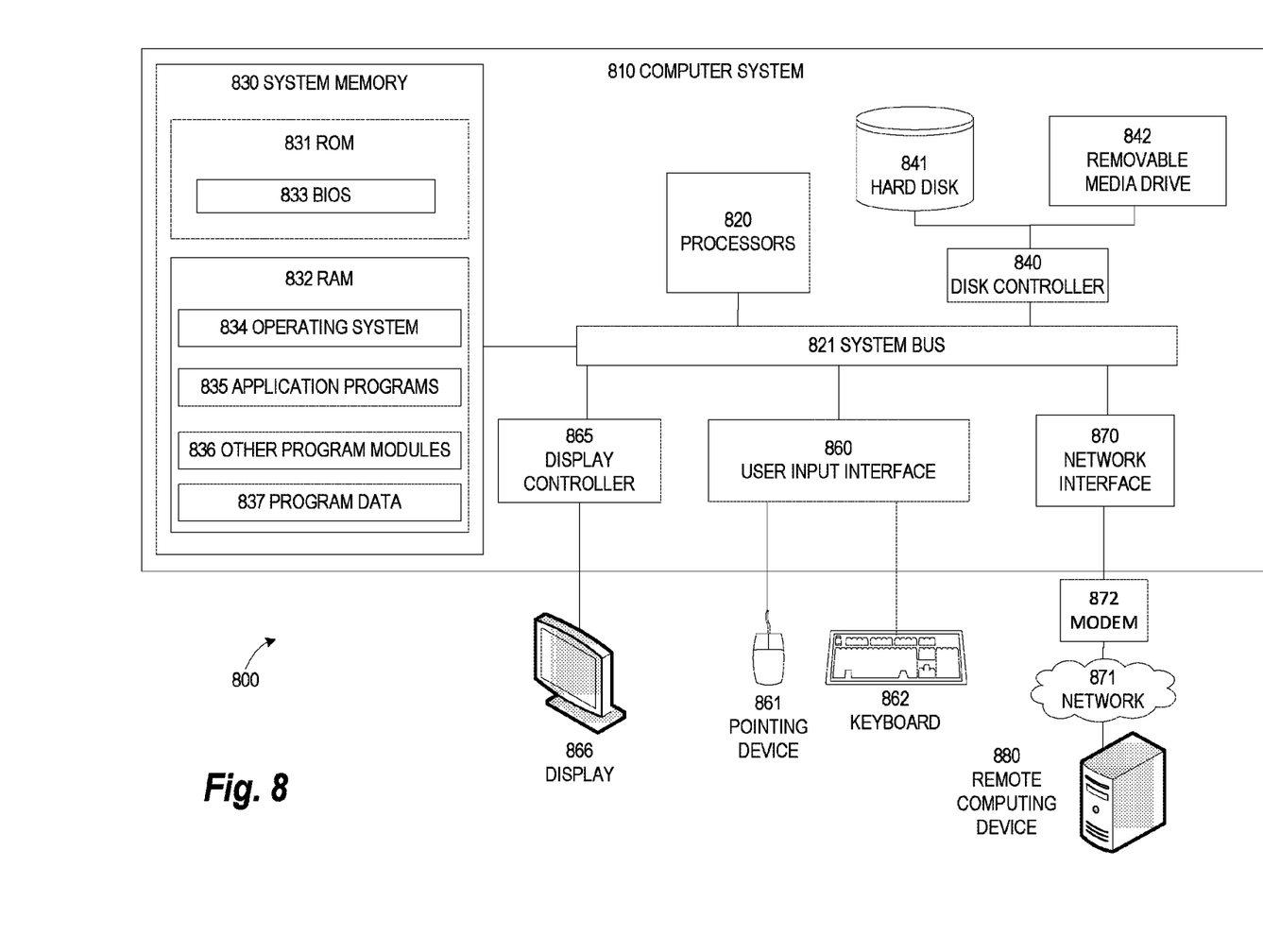
FIG. 8 illustrates an exemplary computing environment within which embodiments of the invention may be implemented.

FIG. 8 illustrates an exemplary computing environment 800 within which embodiments of the invention may be implemented. For example, computing environment 800 may be used to implement one or more components of system 100 shown in FIG. 1. Computers and computing environments, such as computer system 810 and computing environment 800, are known to those of skill in the art and thus are described briefly here.

As shown in FIG. 8, the computer system 810 may include a communication mechanism such as a system bus 821 or other communication mechanism for communicating information within the computer system 810. The computer system 810 further includes one or more processors 820 coupled with the system bus 821 for processing the information.

The processors 820 may include one or more central processing units (CPUs), graphical processing units (GPUs), or any other processor known in the art. More generally, a processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and be conditioned using executable instructions to perform special purpose functions not performed by a general-purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

Continuing with reference to FIG. 8, the computer system 810 also includes a system memory 830 coupled to the system bus 821 for storing information and instructions to be executed by processors 820. The system memory 830 may include computer readable storage media in the form of volatile and/or nonvolatile memory, such as read only memory (ROM) 831 and/or random access memory (RAM) 832. The RAM 832 may include other dynamic storage device(s) (e.g., dynamic RAM, static RAM, and synchronous DRAM). The ROM 831 may include other static storage device(s) (e.g., programmable ROM, erasable PROM, and electrically erasable PROM). In addition, the system memory 830 may be used for storing temporary variables or other intermediate information during the execution of instructions by the processors 820. A basic input/output system 833 (BIOS) containing the basic routines that help to transfer information between elements within computer system 810, such as during start-up, may be stored in the ROM 831. RAM 832 may contain data and/or program modules that are immediately accessible to and/or presently being operated on by the processors 820. System memory 830 may additionally include, for example, operating system 834, application programs 835, other program modules 836 and program data 837.

The computer system 810 also includes a disk controller 840 coupled to the system bus 821 to control one or more storage devices for storing information and instructions, such as a magnetic hard disk 841 and a removable media drive 842 (e.g., floppy disk drive, compact disc drive, tape drive, and/or solid state drive). Storage devices may be added to the computer system 810 using an appropriate device interface (e.g., a small computer system interface (SCSI), integrated device electronics (IDE), Universal Serial Bus (USB), or FireWire).

The computer system 810 may also include a display controller 865 coupled to the system bus 821 to control a display or monitor 866, such as a cathode ray tube (CRT) or liquid crystal display (LCD), for displaying information to a computer user. The computer system includes an input interface 860 and one or more input devices, such as a keyboard 862 and a pointing device 861, for interacting with a computer user and providing information to the processors 820. The pointing device 861, for example, may be a mouse, a light pen, a trackball, or a pointing stick for communicating direction information and command selections to the processors 820 and for controlling cursor movement on the display 866. The display 866 may provide a touch screen interface that allows input to supplement or replace the communication of direction information and command selections by the pointing device 861.

The computer system 810 may perform a portion or all of the processing steps of embodiments of the invention in response to the processors 820 executing one or more sequences of one or more instructions contained in a memory, such as the system memory 830. Such instructions may be read into the system memory 830 from another computer readable medium, such as a magnetic hard disk 841 or a removable media drive 842. The magnetic hard disk 841 may contain one or more datastores and data files used by embodiments of the present invention. Datastore contents and data files may be encrypted to improve security. The processors 820 may also be employed in a multi-processing arrangement to execute the one or more sequences of instructions contained in system memory 830. In alternative embodiments, hard-wired circuitry may be used in place of or in combination with software instructions. Thus, embodiments are not limited to any specific combination of hardware circuitry and software.

As stated above, the computer system 810 may include at least one computer readable medium or memory for holding instructions programmed according to embodiments of the invention and for containing data structures, tables, records, or other data described herein. The term "computer readable medium" as used herein refers to any medium that participates in providing instructions to the processors 820 for execution. A computer readable medium may take many forms including, but not limited to, non-transitory, non-volatile media, volatile media, and transmission media. Non-limiting examples of non-volatile media include optical disks, solid state drives, magnetic disks, and magneto-optical disks, such as magnetic hard disk 841 or removable media drive 842. Non-limiting examples of volatile media include dynamic memory, such as system memory 830. Non-limiting examples of transmission media include coaxial cables, copper wire, and fiber optics, including the wires that make up the system bus 821. Transmission media may also take the form of acoustic or light waves, such as those generated during radio wave and infrared data communications.

The computing environment 800 may further include the computer system 810 operating in a networked environment using logical connections to one or more remote computers, such as remote computing device 880. Remote computing device 880 may be a personal computer (laptop or desktop), a mobile device, a server, a router, a network PC, a peer device or other common network node, and typically includes many or all of the elements described above relative to computer system 810. When used in a networking environment, computer system 810 may include modem 872 for establishing communications over a network 871, such as the Internet. Modem 872 may be connected to system bus 821 via user network interface 870, or via another appropriate mechanism.

Network 871 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 810 and other computers (e.g., remote computing device 880). The network 871 may be wired, wireless or a combination thereof. Wired connections may be implemented using Ethernet, Universal Serial Bus (USB), or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 871.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine-readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity. Also, while some method steps are described as separate steps for ease of understanding, any such steps should not be construed as necessarily distinct nor order dependent in their performance.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A computer-implemented method for scoring a population of examples subject to an additional constraint of a fixed aggregate resource expenditure, the method comprising:

generating a master gain ratio list that identifies, for each example in the population of examples, an attribute combination having a largest gain ratio among all attribute combinations in the example, wherein the master gain ratio list is generated using an iterative process comprising:

identifying a plurality of attribute combinations associated with the example, wherein for each attribute combination of the plurality of attribute combinations at least one attribute in the attribute combination indicates a resource expenditure for the attribute combination, using a predictive model to determine a predicted gain value for each attribute combination, determining a gain ratio for each attribute combination, wherein the gain ratio for an attribute combination is defined as the predicted gain value for the attribute combination divided by the resource expenditure for the attribute combination;

identifying a particular attribute combination in the plurality of attribute combinations having the largest gain ratio, and adding the particular attribute combination and the largest gain ratio to the master gain ratio list;

sorting, by the computer system, the master gain ratio list according to the gain ratio; and performing the resource expenditure associated with a first attribute combination on the sorted master gain ratio list.

2. The method of claim 1, further comprising:

after the iterative process is complete, removing any item from the master gain ratio list corresponding to a resource expenditure exceeding a predetermined constraint.

3. The method of claim 1, wherein the population of examples comprises a plurality of continuous feature values and the method comprises:

binning the plurality of continuous feature values into equal intervals, yielding a plurality of bins, wherein the iterative process is applied to each of the plurality of bins.

4. The method of claim 1, wherein the iterative process further comprises:

for each attribute combination of the plurality of attribute combinations, adjusting the gain ratio based on a monetary cost associated with performing the resource expenditure indicated by the attribute combination.

5. The method of claim 1, wherein the iterative process further comprises:

determining a cost for each individual value associated with feature-value pairs included in the example; and for each of the plurality of attribute combinations, adjusting the gain ratio based on the cost corresponding to values associated with feature-value pairs in the attribute combination.

6. The method of claim 1, wherein the iterative process further comprises:

for each of the plurality of attribute combinations, using a cost function associated with achieving and not achieving a goal to determine a goal probability estimation; and adjusting the gain ratio associated with each attribute combination based on the corresponding goal probability estimation.

7. A system for scoring a population of examples subject to an additional constraint of a fixed aggregate resource expenditure, the system comprising:

one or more processors; and a non-transitory, computer-readable storage medium in operable communication with the one or more processors, wherein the computer-readable storage medium contains one or more programming instructions that, when executed, cause the processors to:

generate a master gain ratio list that identifies, for each example in the population of examples, an attribute combination having a largest gain ratio among all attribute combinations in the example, wherein the master gain ratio list is generated-using an iterative process comprising:

identifying a plurality of attribute combinations associated with the example, wherein for each attribute combination of the plurality of attribute combinations at least one attribute in the attribute combination indicates a resource expenditure for the attribute combination, using a predictive model to determine a predicted gain value for each attribute combination, determining a gain ratio for each attribute combination, wherein the gain ratio for an attribute combination is defined as the predicted gain value for the attribute combination divided by the resource expenditure for the attribute combination, identifying a particular attribute combination in the plurality of attribute combinations having a largest gain ratio, and adding the particular attribute combination and the largest gain ratio to the master gain ratio list;

sort the master gain ratio list according to the gain ratio; and perform the resource expenditure associated with a first attribute combination on the sorted master gain ratio list.

8. The system of claim 7, further comprising:
after the iterative process is complete, removing any item from the master gain ratio list corresponding to a resource expenditure exceeding a predetermined constraint.

9. The system of claim 7, wherein the population of examples comprises a plurality of continuous feature values and the system comprises:

binning the plurality of continuous feature values into equal intervals, yielding a plurality of bins, wherein the iterative process is applied to each of the plurality of bins.

10. The system of claim 7, wherein the iterative process further comprises:

for each attribute combination of the plurality of attribute combinations, adjusting the gain ratio based on a monetary cost associated with performing the resource expenditure indicated by the attribute combination.

11. The system of claim 7, wherein the iterative process further comprises:

determining a cost for each individual value associated with feature-value pairs included in the example; and for each of the plurality of attribute combinations, adjusting the gain ratio based on the cost corresponding to values associated with feature-value pairs in the attribute combination.

12. The system of claim 7, wherein the iterative process further comprises:

for each of the plurality of attribute combinations, using a cost function associated with achieving and not achieving a goal to determine a goal probability estimation; and adjusting the gain ratio associated with each attribute combination based on the corresponding goal probability estimation.

* * * * *